United States Patent
Bhosale et al.

(10) Patent No.: US 10,463,877 B2
(45) Date of Patent: Nov. 5, 2019

(54) LED-BASED PHOTOTHERAPY PANEL CAPABLE OF FITTING IN AN X-RAY CASSETTE TRAY OF AN INCUBATOR

(71) Applicant: KONINKLIJKE PHILIPS N.V., Eindhoven (NL)

(72) Inventors: Pritam Bhosale, Bangalore (IN); Anil Shivram Raiker, Bangalore (IN); Shrutin Ulman, Bangalore (IN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 70 days.

(21) Appl. No.: 14/418,128

(22) PCT Filed: Aug. 6, 2013

(86) PCT No.: PCT/IB2013/056444
§ 371 (c)(1),
(2) Date: Jan. 29, 2015

(87) PCT Pub. No.: WO2014/024140
PCT Pub. Date: Feb. 13, 2014

(65) Prior Publication Data
US 2015/0209598 A1    Jul. 30, 2015

(30) Foreign Application Priority Data
Aug. 8, 2012 (IN) .......................... 3259/CHE/2012

(51) Int. Cl.
*A61N 5/06*    (2006.01)
*A61G 11/00*    (2006.01)
(Continued)

(52) U.S. Cl.
CPC ............ *A61N 5/0621* (2013.01); *A61G 11/00* (2013.01); *A61G 2203/46* (2013.01); *A61G 2210/50* (2013.01); *A61N 2005/0627* (2013.01); *A61N 2005/0637* (2013.01);
(Continued)

(58) Field of Classification Search
CPC ................................................... A61N 5/0621
See application file for complete search history.

(56) References Cited

U.S. PATENT DOCUMENTS 3,877,437 A * 4/1975 Maitan ................ A61N 5/0621
250/455.11
6,045,575 A * 4/2000 Rosen ................ A61N 5/0621
2/905
(Continued)

FOREIGN PATENT DOCUMENTS

CN    201350186 Y    11/2009
GB    2216012 A    10/1989
(Continued)

OTHER PUBLICATIONS

M. Maisels and A. McDonagh, "Phototherapy for Neonatal Jaundice", New England Journal of Medicine, vol. 358, No. 9, pp. 920-928, 2008.*
(Continued)

*Primary Examiner* — Lynsey C Eiseman
*Assistant Examiner* — Amanda L Steinberg

(57) ABSTRACT

Systems and methods for providing phototherapy to infants use a LED-based phototherapy panel designed to fit in an X-ray cassette tray of an incubator.

23 Claims, 5 Drawing Sheets

(52) U.S. Cl.
CPC .......... *A61N 2005/0638* (2013.01); *A61N 2005/0652* (2013.01); *A61N 2005/0663* (2013.01)

(56) References Cited

U.S. PATENT DOCUMENTS

| | | | | |
|---|---|---|---|---|
| 6,350,275 | B1* | 2/2002 | Vreman | A61M 21/00 607/88 |
| 6,356,684 | B1* | 3/2002 | Patterson | G02B 6/2932 385/123 |
| 6,402,681 | B1* | 6/2002 | McDonough | A61N 5/0621 362/130 |
| 6,596,016 | B1* | 7/2003 | Vreman | A61N 5/0621 128/903 |
| 6,712,481 | B2* | 3/2004 | Parker | A61M 21/02 362/330 |
| 6,761,683 | B2* | 7/2004 | Gryn | A61G 11/00 5/603 |
| 7,305,163 | B2* | 12/2007 | Williams | A61N 5/0621 385/45 |
| 8,337,538 | B1* | 12/2012 | Ford | A61N 5/0621 607/88 |
| 2002/0143233 | A1* | 10/2002 | Donnelly | A61F 7/00 600/22 |
| 2004/0236174 | A1* | 11/2004 | Boone | A61B 5/02055 600/21 |
| 2006/0089546 | A1 | 4/2006 | Mahony et al. | |
| 2006/0100675 | A1* | 5/2006 | Gardner | A61N 5/0621 607/88 |
| 2006/0217787 | A1* | 9/2006 | Olson | A61N 5/0616 607/88 |
| 2007/0027510 | A1* | 2/2007 | Rodrigues | A61N 5/0621 607/88 |
| 2010/0222638 | A1* | 9/2010 | Chilton, III | A61G 11/00 600/22 |
| 2010/0286471 | A1* | 11/2010 | Matsubara | A61G 11/00 600/22 |
| 2012/0124750 | A1* | 5/2012 | Pezzani | A61G 7/05 5/658 |
| 2013/0342691 | A1* | 12/2013 | Lewis | H04N 5/332 348/143 |

FOREIGN PATENT DOCUMENTS

| | | |
|---|---|---|
| JP | 2012514498 A | 6/2012 |
| WO | 2006135865 A2 | 12/2006 |
| WO | 2011153599 A1 | 12/2011 |

OTHER PUBLICATIONS

Wentworth, "Neonatal Phototherapy—Today's Lights, Lamps and Devices", Infant, vol. 1, No. 1, 2005, pp. 14-19.

Moreno et al, "Designing Light-Emitting Diode Arrays for Uniform Near-Field Irradiance", Applied Optics, vol. 45, No. 10, Apr. 1, 2006, pp. 2265-2272.

Author Unknown, "Management of Hyperbilirubimemia in the Newborn Infant 35 or More Weeks of Gestation", American Academy of Pediatrics, Clinical Practice Guidelines, Pediatrics, vol. 114, No. 1, 2004, pp. 297-316.

\* cited by examiner

LED-BASED PHOTOTHERAPY PANEL CAPABLE OF FITTING IN AN X-RAY CASSETTE TRAY OF AN INCUBATOR

CROSS-REFERENCE TO PRIOR APPLICATIONS

This application is the U.S. National Phase application under 35 U.S.C. § 371 of International Application No. PCT/IB2013/056444, filed on Aug. 6, 2013, which claims the benefit of Indian Patent Application No. 3259/CHE/2012, filed on Aug. 8, 2012. These applications are hereby incorporated by reference herein.

The present disclosure pertains to systems and methods for providing phototherapy to infants in an incubator or baby warmer, and, in particular, to systems and methods that provide a panel of light emitting diodes that is suitable to fit in an X-ray cassette tray of an incubator or baby warmer.

It is well known to treat infants, e.g. neonates, with phototherapy. An example of well-known phototherapy is jaundice treatment using blue light. It is well known to use an incubator or baby warmer for infants, e.g. neonates, in intensive care environments or elsewhere, e.g. to maintain an environment with an appropriate temperature and/or humidity.

Accordingly, it is an object of one or more embodiments of the present invention to provide a phototherapy panel. The panel comprises a housing and one or more light sources. The housing is configured to carry the one or more light sources. The housing has a light emitting surface that is transparent or translucent, and the housing has a height of less than about 3 cm, a width of less than about 35 cm, and a length of less than about 45 cm. The one or more light sources are configured such that, responsive to activation of one or more light sources and responsive to the phototherapy panel being arranged in suitable proximity to an infant, electromagnetic radiation emitted by the one or more light sources is guided through the light emitting surface of the housing to provide phototherapy to the infant, wherein the one or more light sources are carried by the housing.

It is yet another aspect of one or more embodiments of the present invention to provide a method of providing phototherapy to an infant that is positioned above a transparent or translucent light emitting surface of an infant-supporting body, wherein the infant-supporting body includes a cavity disposed underneath the transparent or translucent light emitting surface. The method comprises providing a housing within the cavity, wherein the housing has a transparent or translucent light emitting surface, wherein the housing has a height of less than about 3 cm, a width of less than about 35 cm, and a length of less than about 45 cm; activating one or more light sources, the light sources being carried by the housing; emitting, by one or more light sources carried by the housing, electromagnetic radiation responsive to activation of the one or more light sources; and guiding the electromagnetic radiation, via the transparent or translucent light emitting surface of the housing, through the transparent or translucent light emitting surface of the infant-supporting body to provide phototherapy to the infant It is yet another aspect of one or more embodiments to provide a system configured to provide phototherapy to an infant that is positioned above a transparent or translucent light emitting surface of an infant-supporting body, wherein the infant-supporting body includes a cavity disposed underneath the transparent or translucent light emitting surface. The system comprises emission means, housing means, housing-supporting means, and means for guiding electromagnetic radiation. The emission means is for emitting electromagnetic radiation. The housing means is for carrying the emission means. The housing means has a transparent or translucent light emitting surface, and a height of less than about 3 cm, a width of less than about 35 cm, and a length of less than about 45 cm. The housing-supporting means is for encompassing and supporting the housing means. The housing-supporting means has a height of at least about 3 cm, a width of at least about 35 cm, and a length of at least about 45 cm. The means for guiding the electromagnetic radiation guides the electromagnetic through the transparent or translucent light emitting surface of the infant-supporting means to provide phototherapy to the infant.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 3:
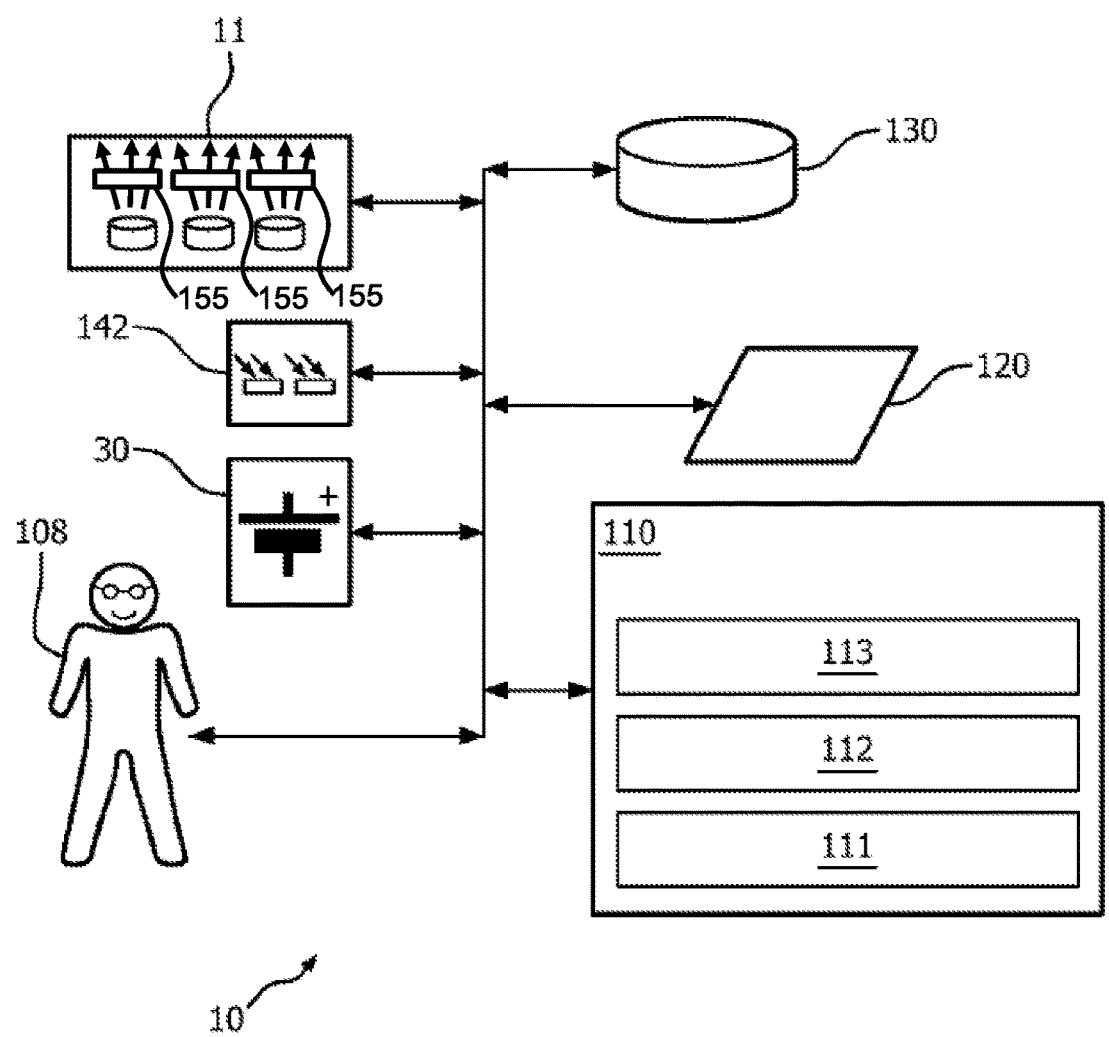
Figure 4:
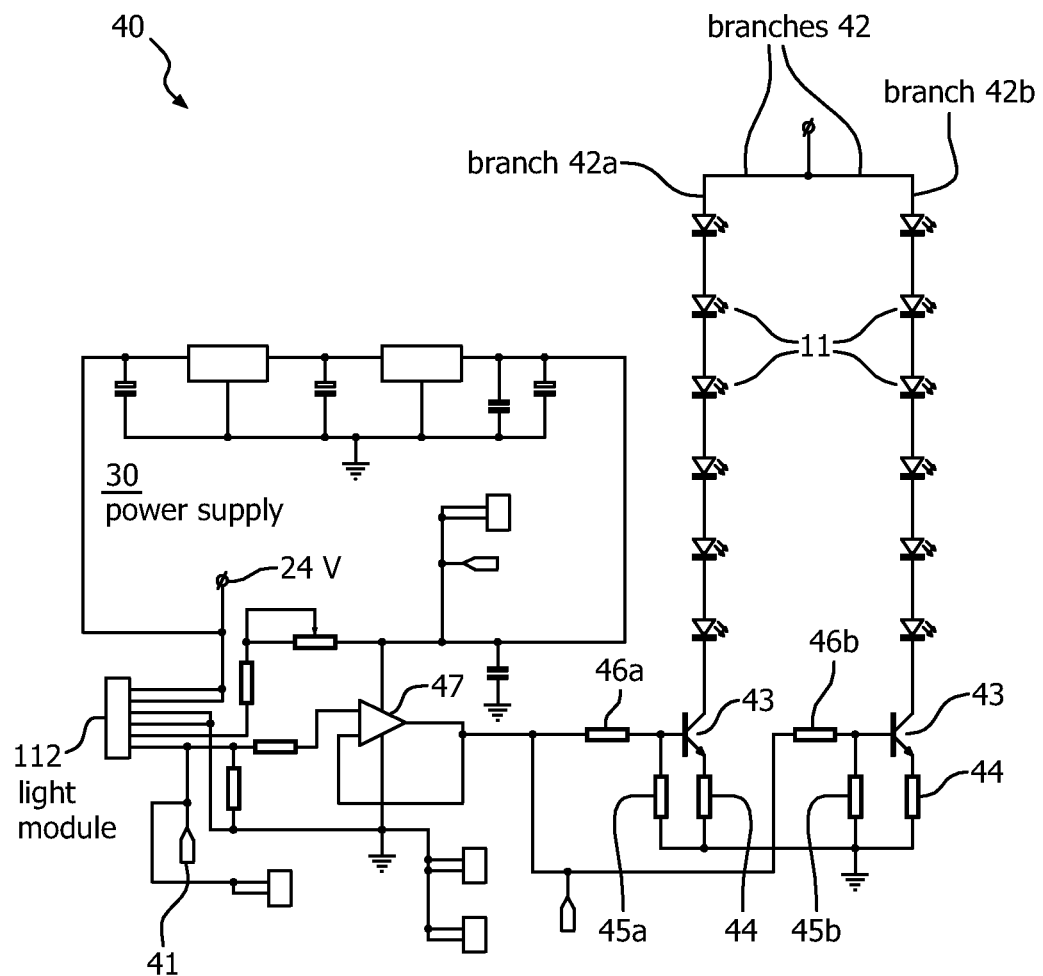
Figure 5:
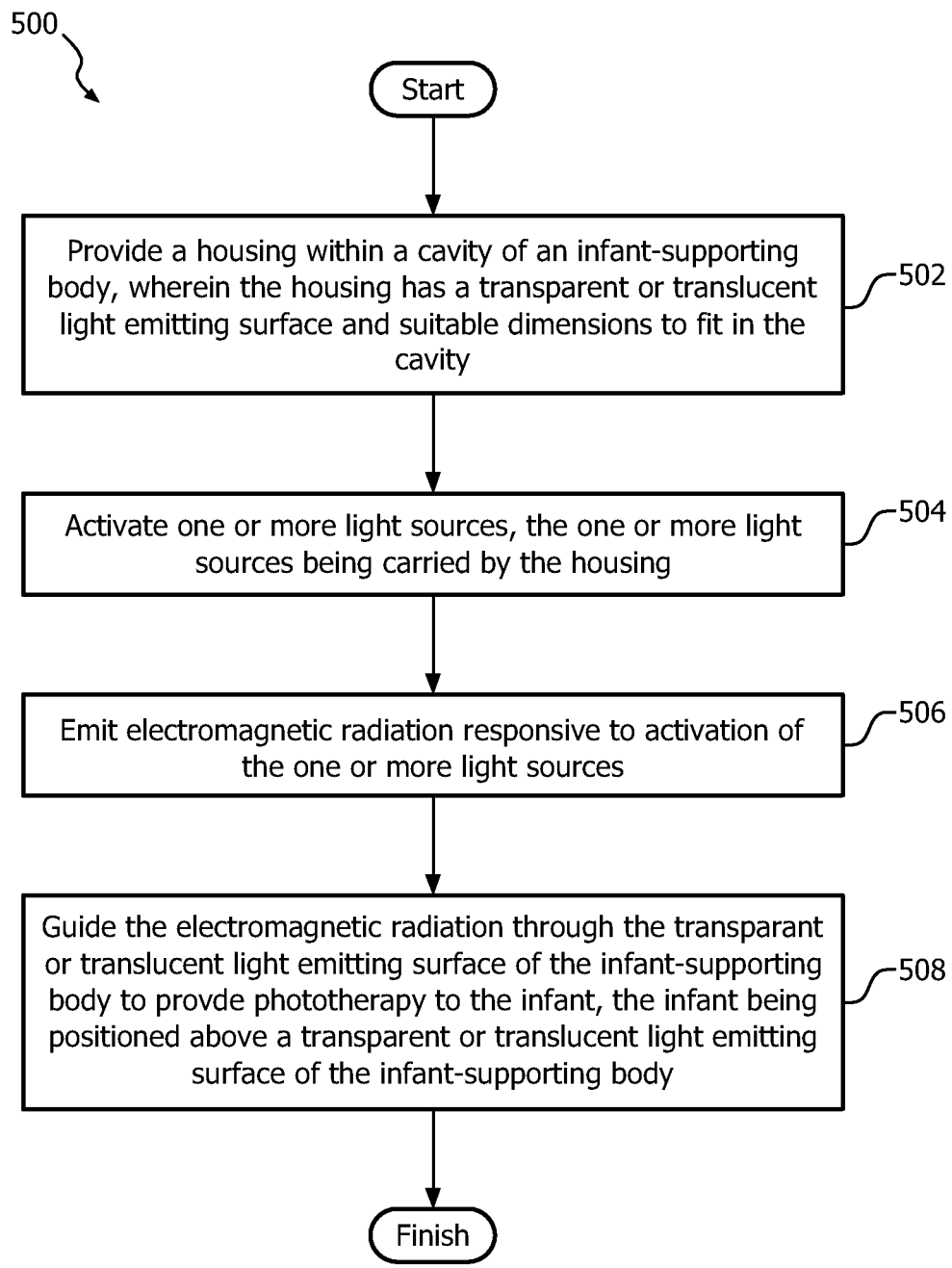

FIG. 3 schematically illustrates a phototherapy panel in accordance with one or more embodiments; and FIG. 4 illustrates a circuit diagram for a phototherapy panel in accordance with one or more embodiments; and FIG. 5 illustrates a method for providing phototherapy in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
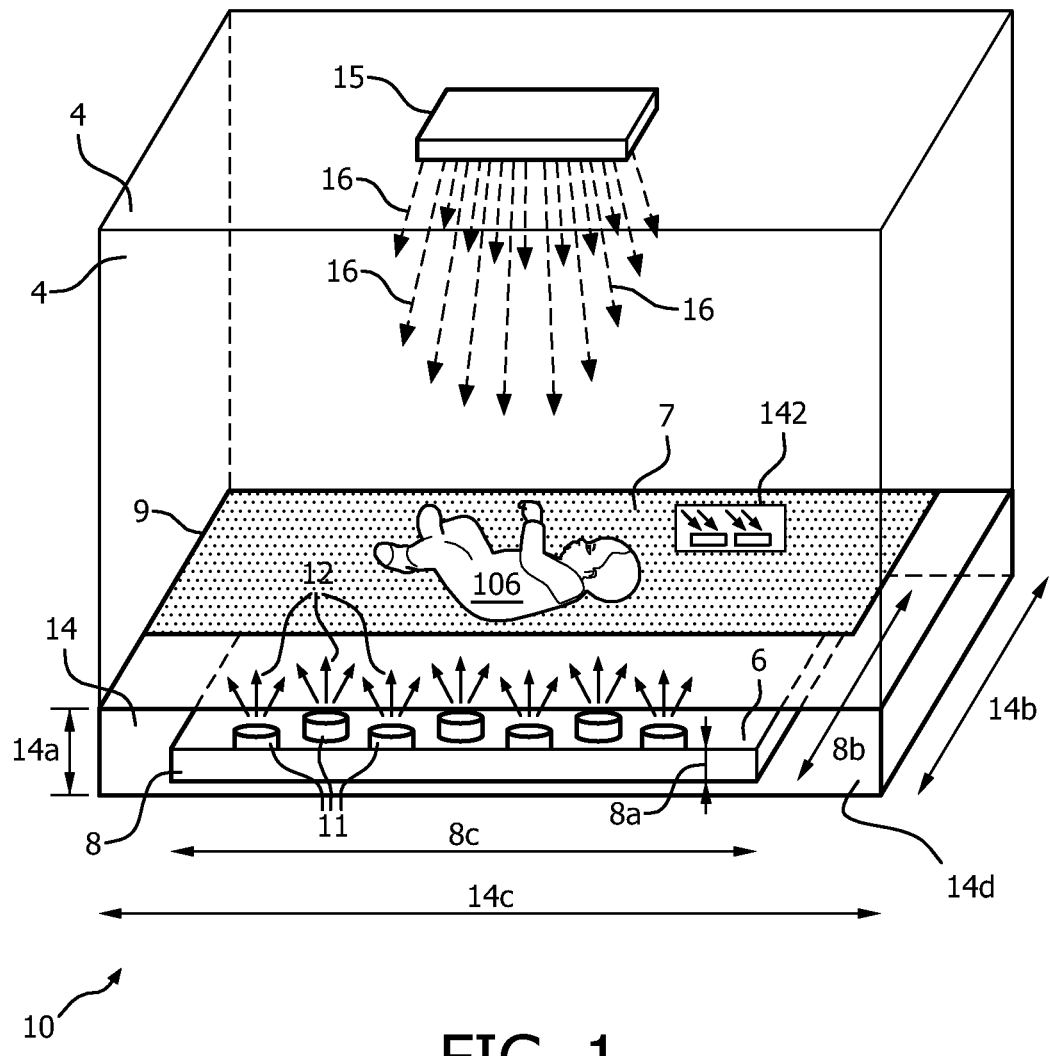
FIG. 1 illustrates a schematic view of a phototherapy panel in accordance with one or more embodiments.

FIG. 1 illustrates a phototherapy panel 10 for providing phototherapy to an infant 106. Phototherapy panel 10 may interchangeably be referred to as system 10. System 10 can be integrated, embedded, incorporated, combined, and/or otherwise operating in conjunction with an incubator 4 or a baby warmer 4 (collectively referred to as incubator 4), an X-ray tube 15, and/or other components. Incubator 4 may include an infant-supporting body 9, X-ray tube 15, and/or other components. System 10 includes one or more of a housing 8, one or more light sources 11, one or more sensors 142, and/or other components. Components of incubator 4 to modify or control environmental conditions for infant 106 such as temperature and/or humidity are not be depicted in FIG. 1.

Phototherapy can be used to treat jaundice (or hyperbilirubinemia) by reducing the level of bilirubin. Effective and/or appropriate levels of phototherapy may be based on an infant's age, size, weight, and/or other physiological, environmental, and/or infant-specific parameters. Phototherapy uses electromagnetic radiation having a peak wavelength between, e.g., 460 nm and 500 nm, an emission spectrum ranging from, e.g., 400 nm to 520 nm, and preferably using a narrow bandwidth delivered at an irradiance of, e.g., 15-35 $\mu W/cm^2/nm$ to, e.g., up to 80% of an infant's body surface area (BSA). Phototherapy may potentially need to be kept from directly impinging on the eyes of the infant, e.g. by making the infant wear goggles. Exposure to the type of blue light that is effective for jaundice treatment may have side-effects for caregivers, including, but not limited to, headache, nausea, and/or vertigo.

Infant-supporting body 9 includes a transparent or translucent light emitting surface 7 and is configured such that infant 106 is positioned above and/or supported on a transparent or translucent light emitting surface 7 during operation. Transparent or translucent light emitting surface 7 engages infant 106 during use of system 10. In other words, infant 106 is placed on transparent or translucent light emitting surface 7 during use of incubator 4 and/or system 10. Infant-supporting body 9 and/or incubator 4 may include a cavity 14. Cavity 14 is disposed and/or positioned underneath transparent or translucent light emitting surface 7 of infant-supporting body 9. In some embodiments, infant-supporting body 9 and/or incubator 4 are not connected to phototherapy panel 10, though these components may operate in concert.

Housing 8 of system 10 includes a transparent or translucent light emitting surface 6. The height, width, and length of housing 8 are referred to as panel height 8a, panel width 8b, and panel length 8c. Housing 8 includes one or more light sources 11 that are carried by housing 8. The one or more light sources 11 emit electromagnetic radiation 12 upon activation, which is guided through transparent or translucent light emitting surface 6. Electromagnetic radiation 12 impinges on infant 106 and thus provide phototherapy for infant 106 during operation of system 10. In some embodiments, housing 8 includes heat-dissipation features (not shown in FIG. 1) to dissipate heat and/or other energy from housing 8. For example, the one or more light sources 11 can generate heat during operation. Heat-dissipation features include one or more of louvers, a fan, and/or other heat-dissipation features. Infant 106 may be monitored while on or near system 10 or a component thereof, e.g. while undergoing phototherapy.

X-ray tube 15 of incubator 4 may emit electromagnetic radiation 16, which is used for imaging purposes, for example in conjunction with an X-ray cassette (not shown in FIG. 1) that is placed in cavity 14 for this purpose. The height, width, and length of cavity 14 are referred to as cavity height 14a, cavity width 14b, and cavity length 14c.

Cavity 14 may be accessible through one or more open sides and/or sides that are configured to be opened and closed when using X-ray tube 15 and/or incubator 4. For example, cavity 14 has at least one open side 14d (also referred to as the front side of cavity 14) to easily insert and remove an X-ray cassette and/or housing 8. Cavity 14 may also be referred to as cassette tray 14 or X-ray cassette tray 14. As depicted in FIG. 1, housing 8 fits in cavity 14, for example by insertion through open side 14d. In other words, at least some dimensions of housing 8 are smaller than the corresponding dimensions of cavity 14, for a particular embodiment of phototherapy panel 10 operating in conjunction with a particular embodiment of an incubator 4 having a cassette tray 14. If at least panel height 8a and one or both of panel width 8b and/or panel length 8c are smaller than cavity height 14a and the shortest of cavity width 14b and cavity length 14c, respectively, then some or all of housing 8 will fit in cavity 14.

As depicted in FIG. 1, panel width 8b is smaller than panel length 8c. This is not intended to be limiting in any way. As depicted in FIG. 1, the open side 14d of cavity 14 is the front side. This is not intended to be limiting in any way. The dimensions of housing 8 are intended to allow housing 8 to fit in different size cavities or cassette trays, e.g. for incubators of different size and/or type. In preferred embodiments, all dimensions of housing 8 are smaller than the corresponding dimensions of cavity 14 such that housing 8 fits into cavity 14 in its entirety.

Cavity height 14c may be at least about 2 cm, at least about 3 cm, at least about 4 cm, between 2 cm and 5 cm, between 3 cm and 6 cm, at least about 1 inch, at least about 1.5 inch, at least about 2 inches, between 1 inch and 2.5 inches, between 1.5 inches and 3 inches, and/or another height. Cavity width 14b may be at least about 30 cm, at least about 35 cm, at least about 40 cm, at least about 45 cm, between 25 cm and 40 cm, between 30 cm and 50 cm, at least about 12 inches, at least about 14 inches, at least about 16 inches, at least about 18 inches, between 10 inches and 16 inches, between 12 inches and 20 inches, and/or another width. Cavity length 14c may be at least about 35 cm, at least about 40 cm, at least about 45 cm, at least about 50 cm, between 30 cm and 45 cm, between 35 cm and 55 cm, at least about 14 inches, at least about 16 inches, at least about 18 inches, at least about 20 inches, between 12 inches and 18 inches, between 14 inches and 22 inches, and/or another length.

Panel height 14c may be less than about 2 cm, less than about 3 cm, less than about 4 cm, between 2 cm and 5 cm, between 3 cm and 6 cm, less than about 1 inch, less than about 1.5 inch, less than about 2 inches, between 1 inch and 2.5 inches, between 1.5 inches and 3 inches, and/or another height. Panel width 14b may be less than about 30 cm, less than about 35 cm, less than about 40 cm, less than about 45 cm, between 25 cm and 40 cm, between 30 cm and 50 cm, less than about 12 inches, less than about 14 inches, less than about 16 inches, less than about 18 inches, between 10 inches and 16 inches, between 12 inches and 20 inches, and/or another width. Panel length 14c may be less than about 35 cm, less than about 40 cm, less than about 45 cm, less than about 50 cm, between 30 cm and 45 cm, between 35 cm and 55 cm, less than about 14 inches, less than about 16 inches, less than about 18 inches, less than about 20 inches, between 12 inches and 18 inches, between 14 inches and 22 inches, and/or another length.

One or more light sources 11 of system 10 in FIG. 1 are configured such that electromagnetic radiation 12 emitted by the one or more light sources is guided through transparent or translucent light emitting surface 6 of housing 8. Individual light sources include one or more of a light-emitting diode (LED), an organic light-emitting diode (OLED), and/ or other source of electromagnetic radiation. Light sources 11 are arranged in a regular pattern, irregular pattern, or combination of both. For example, light sources 11 may be arranged in a regular grid. The grid includes N rows and M columns, wherein N and M may number between 2 and 40, and/or between other numbers. In a preferred embodiment, N and M are 6 and 21. In some embodiments, light sources 11 are arranged in a regular and/or off-set grid to provide uniform electromagnetic radiation and/or phototherapy.

Figure 2:
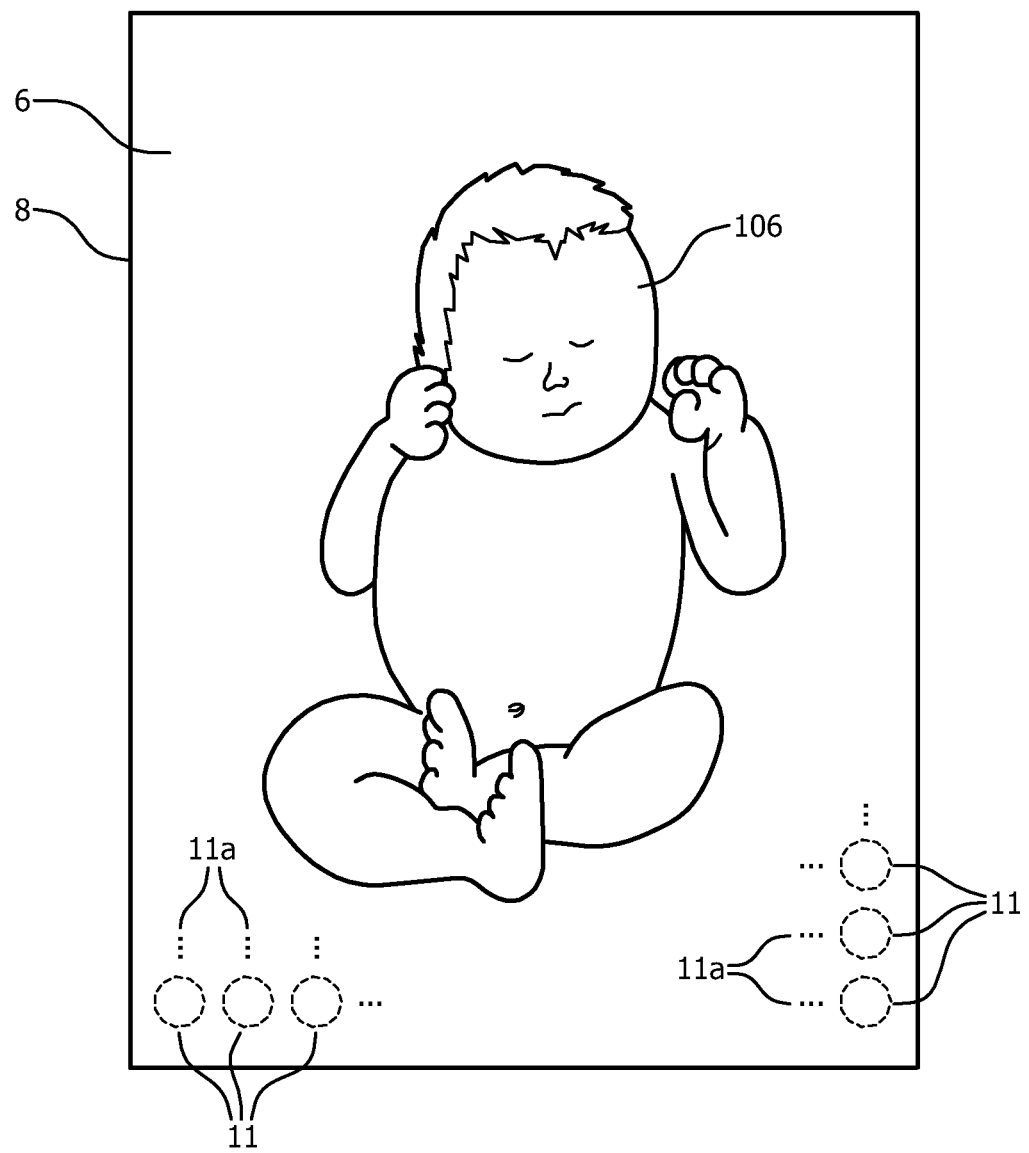
FIG. 2 illustrates a top view of a phototherapy panel in accordance with one or more embodiments.

By way of illustration, FIG. 2 illustrates a top-view of system 10. The depiction of three light sources 11 underneath the bottom left corner of top-surface 7 is not meant to be limiting, but to be exemplary. The depiction of three light sources 11 underneath the bottom right corner of top-surface 7 is not meant to be limiting, but to be exemplary. Ellipses 11a indicate additional light sources that may be arranged underneath top-surface 7, horizontally, vertically, diagonally, and/or in multiple directions, e.g. to create a regular grid of light sources. Light sources 11 may extend underneath the entire top-surface 7 of infant-supporting body 6, including under infant 106.

Referring to FIG. 1, light sources 11 of system 10 are configured to have one or more of a controllable level of intensity (e.g. denoted by a percentage of the maximum available level of intensity for an individual light source), a controllable direction and/or angle of illumination (as depicted by multiple directions of electromagnetic radiation 12 for individual light sources in FIG. 1), a controllable selection of illumination spectra, and/or other controllable illumination characteristics and/or illumination parameters. For example, illumination parameters of a light source 11 may be controlled by adjusting optical components 155 within the light source, including, but not limited to, one or more of refractive components, reflective components, lenses, mirrors, filters, polarizers, diffraction gradients, optical fibers, and/or other optical components. Individual light sources 11 may be controlled such that only part of (the exposed skin of) infant 106 is illuminated.

Note that electromagnetic radiation emitted by real-world light sources, as opposed to theoretical models of light sources, has a non-deterministic distribution of its intensity and/or (beam) direction, at least for practical applications of phototherapy and/or digital image processing. Note furthermore that guiding, reflecting, and/or scattering a beam of electromagnetic radiation is considered a stochastic event governed by a probability distribution. Nonetheless, electromagnetic radiation is considered to substantially directly impinge on or near a particular surface and/or location if at least about 90%, at least about 95%, about 99%, and/or another percentage of the emitted radiation directly so impinges.

Sensor(s) 142 of system 10 in FIG. 1 and/or other figures are configured to generate output signals conveying information related to one or more parameters of electromagnetic radiation 12 emitted by one or more light sources 11. Parameters of electromagnetic radiation may include one or more of peak wavelength, wavelength band, emission spectrum, bandwidth, irradiance, luminance, intensity and/or other parameters of electromagnetic radiation. Alternatively, and/or simultaneously, one or more output signals may convey information related to the age, position, posture, size, weight, and/or status of infant 106, physiological, environmental, and/or infant-specific (medical) parameters related to infant 106, and/or other information. System 10 may use any of the generated output signals as feedback to control operations of system 10, and/or to monitor infant 106. In some embodiments, the conveyed information is related to parameters associated with the state and/or condition of infant 106, the breathing of infant 106, the gas breathed by infant 106, the heart rate of infant 106, the respiratory rate of infant 106, vital signs of infant 106, including one or more temperatures, whether peripheral or central, and/or other parameters. Individual sensors or subsets of sensors from sensors 142 may be designated by specific functions, such as, e.g., an irradiance sensor, a light sensor, a temperature sensor, a flux sensor, and/or other sensors.

As a non-limiting example, one or more sensors 142 generate one or more output signals conveying information related to a (three-dimensional) position of infant 106 on transparent or translucent light emitting surface 7, e.g. through stereoscopy.

In some embodiments, sensors 142 are configured to generate output signals conveying information related to a level of bilirubin in infant 106. Such sensors can be used to perform interstitial fluids bilirubin measurements.

The illustration of sensor 142 including two members in FIG. 1 is not intended to be limiting. System 10 may include one or more sensors. Resulting signals or information from one or more sensors 142 are transmitted to other components of system 10. This transmission can be wired and/or wireless. Monitoring of infant 106 and/or the environment near infant 106 may be based on one or more sensors 142 and/or any of the related parameters described herein. Monitoring and/or measuring may be used as a contact-less, non-invasive means to obtain information. "Contact-less" refers to either refraining from the use of adhesives (e.g. on the skin of infant 106) and/or refraining from direct skin contact in the context of this disclosure. Note that any sensor described herein can be contact-less.

In some embodiments, the function of system 10 needs to be accomplished within an incubator environment, such that the micro-climate within the incubator (including one or more of an internal temperature, humidity, and/or other characteristics of a micro-climate within an incubator), e.g. incubator 4, is left substantially undisturbed during phototherapy. By way of illustration, FIG. 3 illustrates a system 10 for provide phototherapy for an infant, that may be embedded within incubator 4. As depicted in FIG. 3, system 10 includes, in addition to any previously mentioned components in this disclosure, one or more of one or more light sources 11, one or more sensors 142, a power supply 30, electronic storage 130, a user interface 120, one or more processors or controllers 110 (collectively referred to herein as processor 110), a parameter determination module 111, a light module 112, a therapy module 113, and/or other components.

Power supply 30 is configured to supply current and/or power to one or more light sources 11. In preferred embodiments, power supply 30 is configured to supply direct current rather than alternating current to the one or more light sources 11. By supplying direct current to the one or more light sources 11 upon activation of system 10, electromagnetic interference (EMI), particularly EMI having radio frequencies (RF) may be reduced compared to phototherapy systems that use alternating currents to power one or more light sources.

User interface 120 of system 10 in FIG. 3 is configured to provide an interface between system 10 and user 108 through which the user can provide information to and/or receive information from system 10. This enables data, results, and/or instructions and any other communicable items, collectively referred to as "information," to be communicated between the user and system 10. An example of information that can be conveyed to user 108 is the current intensity level of phototherapy, and/or the elapsed time since phototherapy commenced. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source includes, for example, one or more of at least one LED, at least one light bulb, a display screen, and/or other sources. User interface 120 controls the radiation source to emit light in a manner that conveys information to user 108.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Electronic storage 130 of system 10 in FIG. 3 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information related to the provided phototherapy, and/or other information. Electronic storage 130 may be a separate component within system 10, or is provided integrally with one or more other components of system 10 (e.g., processor 110).

Processor 110 of system 10 in FIG. 3 is configured to provide information processing and control capabilities in system 10. As such, processor 110 includes one or more of a digital processor, a microcontroller, an analog processor, a digital circuit designed to process information, an analog circuit designed to process information, a state machine, and/or other mechanisms for electronically processing information. Although processor 110 is shown in FIG. 3 as a single entity, this is for illustrative purposes only. In some implementations, processor 110 includes a plurality of processing units.

As is shown in FIG. 3, processor 110 is configured to execute one or more computer program modules. The one or more computer program modules include one or more of parameter determination module 111, light module 112, therapy module 113, and/or other modules. Processor 110 is configured to execute modules 111, 112 and/or 113 by software; hardware; firmware; some combination of software, hardware, and/or firmware; and/or other mechanisms for configuring processing capabilities on processor 110.

It should be appreciated that although modules 111-113 are illustrated in FIG. 3 as being co-located within a single processing unit, in implementations in which processor 110 includes multiple processing units, one or more of modules 111-113 may be located remotely from the other modules. The description of the functionality provided by the different modules 111-113 described below is for illustrative purposes, and is not intended to be limiting, as any of modules 111-113 may provide more or less functionality than is described. For example, one or more of modules 111-113 may be eliminated, and some or all of its functionality may be provided by other ones of modules 111-113. Note that processor 110 may be configured to execute one or more additional modules that may perform some or all of the functionality attributed below to one of modules 111-113.

Parameter determination module 111 of system 10 in FIG. 3 is configured to determine one or more status parameters, medical parameters, environmental parameters, and/or other parameters from output signals generated by one or more sensors 142. Environmental parameters are related to one or more of the parameters of electromagnetic radiation, various temperatures, humidity level, and/or other environmental parameters, which may be related to environmental conditions near system 10 or within incubator 4. One or more status parameters may be related to an infant's age, size, volume, weight, and/or other infant-specific parameters. One or more status parameters may be related to the presence, posture, and/or position of infant 106. One or more medical parameters may be related to monitored vital signs of infant 106, physiological parameters of infant 106, and/or other medical parameters of infant 106. Some or all of this functionality can be incorporated or integrated into other computer program modules of processor 110.

Light module 112 of system 10 in FIG. 3 is configured to control one or more light sources 11 such that an amount of emitted electromagnetic radiation (in particular electromagnetic radiation 12) is adjustable through one or more settings. The emitted electromagnetic radiation is intended to provide phototherapy for infant 106. Control by light module 112 may be based on individual light sources, one or more subsets of light sources, one or more groups of light sources, one or more rows and/or columns of light sources, and/or any combination thereof. Control by light module 112 includes control of one or more of the controllable level of intensity, the controllable direction and/or angle of illumination, the controllable selection of illumination spectra, and/or other controllable illumination characteristics and/or illumination parameters of one or more light sources 11. Control by light module 112 may be based on any parameters determined by parameter determination module 111.

In some embodiments, the one or more light sources 11 are controlled using a circuit 40 depicted in FIG. 4. Circuit 40 includes two branches 42 of six light sources 11 each. As depicted in FIG. 4, the one or more light sources 11 are light-emitting diodes (LEDs). This is an exemplary configuration. Individual ones of the branches 42 may correspond to rows and/or columns of a grid (and/or triangular pattern) of LEDs. For example, an implementation of a phototherapy panel using 21 rows and/or columns of LEDs may be implemented by extending circuit 40 to include 21 branches.

Operation of circuit 40 is adjustable to at least two settings, for moderate and high levels of intensity of the phototherapy. For example, a moderate level of intensity may correspond to 15 $\mu W/cm^2/nm$, whereas a high level of intensity may correspond to 30 $\mu W/cm^2/nm$ or more. Light sources 11 in circuit 40 are driven by power supply 30, which supplies 24V. Referring to branch 42a (though other branches have similar components), transistor 43 and resistive element 44 in branch 42a control the current through branch 42a. Variation of the base voltage varies the current through branch 42a, and thus through the LEDs therein. The base drive circuit of transistor 43 in branch 42a included a divider including resistive element 45a and resistive element 46a, operating in conjunction with operational amplifier 47, which provides a stable reference voltage at the output of op-amp 47. The control voltage going into op-amp 47 may be supplied, controlled, and/or adjusted by light module 112 and/or by a potentiometer 41. Similarly, the base drive circuit of transistor 43 in branch 42b includes a divider including resistive element 45b and resistive element 46b, operating in conjunction with op-amp 47. Changing the control voltage corresponds to circuit 40 operating in another setting.

In a preferred embodiment of circuit 40 having 21 branches, a control voltage of 3V may correspond to a 20 mA current going through the LEDs, which in turn correspond to the high level of intensity of 30 $\mu W/cm^2/nm$ for the provided phototherapy. Reducing the control voltage corresponds to a different operational setting, with a reduced level of intensity for the provided phototherapy.

In some embodiments, operation of light module 112 is responsive to, and/or controlled by a timer. For example, phototherapy is stopped after a predetermined period of time has elapsed, as indicated by the timer. In some embodiments, the level of intensity of the provided phototherapy is reduced over time, for example gradually from more to less intensive levels (or settings of light module 112 corresponding thereto). For example, control of the level of intensity may be programmed into an algorithm that operates based on one or more of the current intensity level of emitted electromagnetic radiation 12 as determined through a sensor 142, elapsed time of phototherapy according to a timer, prescribed therapy regimen as provided by a caregiver.

Referring to FIG. 3, therapy module 113 of system 10 is configured to determine a recommended phototherapy regimen for infant 106. A phototherapy regimen is based on one or more of the one or more parameters of electromagnetic radiation, one or more of information related to the size/volume/weight of infant 106, information related to the age of infant 106, information related to previously administered phototherapy to infant 106, information related to medical parameters pertaining to the status of infant 106 (e.g. bilirubin measurements), stated and/or provided information and/or instructions from a user 108 or caregiver, clinician input, guidelines, charts, and/or other information. The recommended phototherapy regimen may in turn be used by light module 112 to control the one or more light sources and/or adjust one or more settings of light module 112. In some embodiments, operation of therapy module 113 is responsive to, and/or controlled by a timer in a manner similar to the described usage of a timer related to light module 112.

FIG. 5 illustrates a method 500 for providing phototherapy for an infant that is positioned above a transparent or translucent light emitting surface of an infant-supporting body, wherein the infant-supporting body includes a cavity disposed underneath the transparent or translucent light emitting surface. The operations of method 500 presented below are intended to be illustrative. In some embodiments, method 500 is accomplished with one or more additional operations not described, and/or without one or more of the operations discussed. Additionally, the order in which the operations of method 500 are illustrated in FIG. 5 and described below is not intended to be limiting.

In some embodiments, method 500 is implemented in one or more processing devices (e.g., a digital processor, a microcontroller, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a housing is provided within the cavity, wherein the housing has a transparent or translucent light emitting surface. The housing has a height of less than about 3 cm, a width of less than about 35 cm, and a length of less than about 45 cm, such that the housing fits inside the cavity. In one embodiment, operation 502 is performed by an infant-supporting body and/or cavity thereof similar to or substantially the same as infant-supporting body 9 and/or cavity 14 (shown in FIG. 1 and described above).

At an operation 504, one or more light sources are activated, the one or more light sources being carried by the housing. In one embodiment, operation 504 is performed by a light module similar to or substantially the same as light module 112 (shown in FIG. 3 and described above).

At an operation 506, electromagnetic radiation is emitted responsive to the activation of the one or more light sources. In one embodiment, operation 506 is performed by one or more light sources similar to or substantially the same as one or more light sources 11 (shown in FIG. 1 and described above).

At an operation 508, electromagnetic radiation is guided through the transparent or translucent light emitting surface of the infant-supporting body to provide phototherapy to the infant, the infant being positioned above a transparent or translucent light emitting surface of the infant-supporting body. In one embodiment, operation 508 is performed by a transparent or translucent light emitting surface of the housing similar to or substantially the same as transparent or translucent light emitting surface 6 of housing 8 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A phototherapy system comprising:
an incubator, the incubator having an x-ray cassette tray;
a housing configured to carry one or more light sources, wherein the housing has a light emitting surface that is transparent or translucent, and wherein the housing has a height of 3 cm or less, a width of 35 cm or less, and a length of 45 cm or less such that it fits within the x-ray cassette tray;
one or more light sources configured to respond to activation of the one or more light sources for emitting electromagnetic radiation; and
one or more adjustable, optical components of the one or more light sources configured to be adjusted, via one or more processors, to change a plurality of illumination parameters, the one or more adjustable, optical components being a refractive component, a reflective component, a lens, a mirror, an optical fiber, a polarizer, and/or a diffraction gradient,
wherein the housing is configured relative to the incubator such that, in use, the housing is disposed within the x-ray cassette tray and the emitted electromagnetic radiation travels through the light emitting surface of the housing to impinge on an infant within an environment of the incubator.

2. The phototherapy system of claim 1, further comprising:
a power supply that supplies direct current;
wherein the one or more light sources include one or more light emitting diodes, and wherein the power supply supplies direct current to the one or more light emitting diodes resulting in an intensity of 30 μW/cm2/nm or less upon activation.

3. The phototherapy system of claim 1, wherein the one or more processors are configured to control the one or more light sources such that an amount of emitted electromagnetic radiation is adjustable through one or more settings.

4. The phototherapy system of claim 3, further comprising:
one or more sensors configured to generate one or more output signals conveying information related to one or more parameters of the emitted electromagnetic radiation;
wherein the control of the one or more light sources is based on the one or more generated output signals.

5. The phototherapy system of claim 4, wherein
the one or more processors are further configured to determine a recommended therapy regimen based on information related to the one or more parameters of the emitted electromagnetic radiation;
wherein the control of the one or more light sources is further based on the recommended therapy regimen.

6. The phototherapy system of claim 1, wherein the engagement of the incubator by the housing comprises (i) insertion of the housing through an opening on a first side of the incubator into the x-ray cassette tray, the x-ray cassette tray being disposed underneath a transparent or translucent infant-supporting body, and (ii) emission of the electromagnetic radiation through the transparent or translucent infant-supporting body.

7. The phototherapy system of claim 1, wherein the one or more adjustable, optical components include a filter.

8. The phototherapy system of claim 1, wherein control of an intensity level of the emitted electromagnetic radiation is programmed into an algorithm that operates based on a predetermined therapy regimen prescribed by a caregiver.

9. The phototherapy system of claim 8, further comprising:
a timer; and
one or more sensors configured to generate one or more output signals conveying information related to one or more parameters of the emitted electromagnetic radiation,
wherein the intensity level is further controlled based on a current intensity level of the emitted electromagnetic radiation as determined by the one or more output signals and on an elapsed time of phototherapy provided to the infant according to the timer.

10. The phototherapy system of claim 1, further comprising:
one or more sensors configured to generate one or more output signals conveying information specifying a three-dimensional position or posture of the infant.

11. A method of providing a phototherapy system suitable to treat an infant that is positioned above a first transparent or translucent light emitting surface of an infant-supporting body, the method comprising:
providing an incubator, the incubator having an x-ray cassette tray;
providing a housing within the x-ray cassette tray such that the housing is disposed underneath the first transparent or translucent light emitting surface of the infant-supporting body, wherein the housing has a second transparent or translucent light emitting surface, and wherein the housing has a height of 3 cm or less, a width of 35 cm or less, and a length of 45 cm or less;
carrying, by the housing, one or more light sources such that, upon activation of the one or more light sources, electromagnetic radiation is emitted by the one or more light sources; and
controlling, by one or more processors, a plurality of illumination parameters of the one or more light sources by adjusting one or more adjustable, optical components with respect to the one or more light sources, the one or more adjustable, optical components being a refractive component, a reflective component, a lens, a mirror, an optical fiber, a polarizer, and/or a diffraction gradient,
wherein the housing is configured relative to an incubator such that the emitted electromagnetic radiation travels through the second light emitting surface of the housing and through the first light emitting surface of the infant-supporting body to impinge on the infant within an environment of the incubator.

12. The method of claim 11, further comprising:
supplying direct current by a power supply;
wherein the one or more light sources include one or more light emitting diodes, and wherein the power supply supplies direct current to the one or more light emitting diodes resulting in an intensity of 30 μW/cm2/nm or less upon activation.

13. The method of claim 11, further comprising:
controlling one or more light sources such that an amount of emitted electromagnetic radiation is adjustable.

14. The method of claim 13, further comprising:
generating one or more output signals conveying information related to one or more parameters of the emitted electromagnetic radiation;
wherein controlling the one or more light sources is based on the one or more generated output signals.

15. The method of claim 14, further comprising:
determining a recommended therapy regimen based on information related to the one or more parameters of the emitted electromagnetic radiation;
wherein controlling the one or more light sources is further based on the recommended therapy regimen.

16. The method of claim 11, wherein the engagement of the incubator by the housing comprises (i) insertion of the housing through an opening on a first side of the incubator into the x-ray cassette tray, the x-ray cassette tray being disposed underneath the infant-supporting body, and (ii) emission of the electromagnetic radiation through the infant-supporting body.

17. A system configured to provide phototherapy to an infant that is positioned above a first transparent or translucent light emitting surface of an infant-supporting body, the system comprising:
an incubator means, the incubator means having an x-ray cassette tray;
emission means for emitting electromagnetic radiation;
housing means for carrying the emission means within the x-ray cassette tray, wherein the housing means has a second transparent or translucent light emitting surface, and wherein the housing means has a height of 3 cm or less, a width of 35 cm or less, and a length of 45 cm or less; and
means for controlling a plurality of illumination parameters of the one or more light sources, wherein the illumination parameters controlling means adjusts one or more adjustable, optical components with respect to the one or more light sources, the one or more adjustable, optical components being a refractive component, a reflective component, a lens, a mirror, an optical fiber, a polarizer, and/or a diffraction gradient,
wherein the housing means is configured relative to the incubator means such that, in use, the housing is disposed within the x-ray cassette tray and the emitted electromagnetic radiation travels through the second transparent or translucent light emitting surface of the housing means to impinge on the infant within an environment of the incubator means.

18. The system of claim 17, further comprising:
power supply means for supplying direct current, wherein the power supply means supplies direct current to the emission means resulting in an intensity of 30 µW/cm2/nm or less.

19. The system of claim 17, further comprising:
controlling means for controlling the emission means such that an amount of emitted electromagnetic radiation is adjustable.

20. The system of claim 19, further comprising:
means for generating one or more output signals conveying information related to one or more parameters of the emitted electromagnetic radiation;
wherein operation of the controlling means is based on the one or more generated output signals.

21. The system of claim 20, further comprising;
means for determining a recommended therapy regimen based on information related to the one or more parameters of the emitted electromagnetic radiation;
wherein operation of the controlling means is further based on the recommended therapy regimen.

22. The system of claim 17, wherein the engagement of the incubator means by the housing means comprises (i) insertion of the housing means through an opening on a first side of the incubator means into the x-ray cassette tray and (ii) emission of the electromagnetic radiation through the infant-supporting body.

23. A phototherapy system comprising:
an incubator, the incubator having an x-ray cassette tray;
a housing configured to carry one or more light sources, wherein the housing has a light emitting surface that is transparent or translucent, and wherein the housing has a height of 3 cm or less, a width of 35 cm or less, and a length of 45 cm or less such that it fits within the x-ray cassette tray;
one or more light sources configured to respond to activation of the one or more light sources for emitting electromagnetic radiation; and
one or more adjustable, optical components of the one or more light sources configured to be adjusted, via one or more processors, to change a plurality of illumination parameters, the one or more adjustable, optical components being a refractive component, a reflective component, a lens, a mirror, an optical fiber, a polarizer, and/or a diffraction gradient,
wherein the housing is configured relative to the incubator such that the emitted electromagnetic radiation travels through the light emitting surface of the housing to impinge on an infant within an environment of the incubator wherein the one or more processors are configured to change a direction or angle of illumination of the one or more light sources.

* * * * *